United States Patent
Shan et al.

(10) Patent No.: US 8,729,131 B2
(45) Date of Patent: May 20, 2014

(54) AGOMELATINE HYDROCHLORIDE HYDRATE AND PREPARATION THEREOF

(75) Inventors: Hanbin Shan, Gaoan (CN); Zhedong Yuan, Shanghai (CN); Xueyan Zhu, Shanghai (CN); Peng Zhang, Pudong New Area (CN); Hongjuan Pan, Shanghai (CN); Xiong Yu, Hongkou District (CN)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 13/635,063

(22) PCT Filed: Mar. 17, 2011

(86) PCT No.: PCT/CN2011/071910
§ 371 (c)(1), (2), (4) Date: Sep. 14, 2012

(87) PCT Pub. No.: WO2011/113362
PCT Pub. Date: Sep. 22, 2011

(65) Prior Publication Data
US 2013/0005820 A1    Jan. 3, 2013

(30) Foreign Application Priority Data
Mar. 17, 2010   (CN) .......................... 2010 1 0126254

(51) Int. Cl.
| | | |
|---|---|---|
| *A01N 37/18* | (2006.01) | |
| *A61K 31/16* | (2006.01) | |
| *C07C 233/00* | (2006.01) | |
| *C07C 235/00* | (2006.01) | |
| *C07C 237/00* | (2006.01) | |
| *C07C 239/00* | (2006.01) | |

(52) U.S. Cl.
USPC ........... 514/630; 514/613; 564/123; 564/219; 564/222

(58) Field of Classification Search
USPC ................... 564/123, 219, 222; 514/613, 630
See application file for complete search history.

(56) References Cited

FOREIGN PATENT DOCUMENTS
| | | |
|---|---|---|
| CN | 101481321 | 7/2009 |
| CN | 101643434 | 2/2010 |

OTHER PUBLICATIONS

Kennedy et al. Neuropsychiatric Disease and treatment, 2007, vol. 3 (4), pp. 423-428.*
Arendt et al., The British Journal of Psychiatry, 2008, vol. 193, pp. 267-269.*
International Search Report for PCT/CN2011/071910.
International Preliminary Report on Patentability With Written Opinion of PCT/CN2011/071910 of Jun. 16, 2011.

* cited by examiner

*Primary Examiner* — Kara R McMillian
(74) *Attorney, Agent, or Firm* — Hueschen and Sage

(57) ABSTRACT

The present invention relates to an agomelatine hydrochloride hydrate of formula I, preparation and use thereof, and to pharmaceutical composition containing it. The agomelatine hydrohalide hydrate obtained through the present method has significant increased solubility than agomelatine, and therefore is more suitable for manufacturing pharmaceutical formulations. In addition, the product enjoys higher stability and purity. Using the present method, product of high purity can be obtained through a simple process, free of any complicated steps.

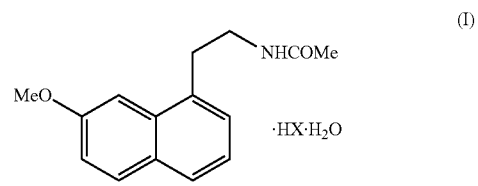

(I)

wherein X is Cl.

16 Claims, 3 Drawing Sheets

| # | 2-Theta | d(Å) | I% |
|---|---------|------|-----|
| 1 | 9.076 | 9.7360 | 11.24 |
| 2 | 10.727 | 8.2408 | 1.67 |
| 3 | 11.404 | 7.7528 | 4.91 |
| 4 | 11.843 | 7.4665 | 4.01 |
| 5 | 13.635 | 6.4887 | 27.62 |
| 6 | 14.427 | 6.1345 | 16.38 |
| 7 | 16.872 | 5.2507 | 34.17 |
| 8 | 18.176 | 4.8767 | 100.00 |
| 9 | 20.187 | 4.3952 | 6.55 |
| 10 | 21.610 | 4.1089 | 62.25 |
| 11 | 22.259 | 3.9905 | 7.94 |
| 12 | 22.794 | 3.8981 | 19.22 |
| 13 | 23.878 | 3.7235 | 31.32 |
| 14 | 24.214 | 3.6726 | 82.40 |
| 15 | 24.827 | 3.5833 | 6.55 |
| 16 | 25.457 | 3.4960 | 41.45 |
| 17 | 25.714 | 3.4617 | 37.06 |
| 18 | 27.430 | 3.2488 | 31.69 |
| 19 | 28.200 | 3.1619 | 6.07 |
| 20 | 29.207 | 3.0551 | 13.75 |
| 21 | 30.036 | 2.9727 | 3.61 |

FIG 2B

| 22 | 30.961 | 2.8860 | 5.72 |
|---|---|---|---|
| 23 | 31.655 | 2.8242 | 9.86 |
| 24 | 32.523 | 2.7508 | 1.32 |
| 25 | 33.389 | 2.6814 | 6.50 |
| 26 | 34.380 | 2.6063 | 3.39 |
| 27 | 35.027 | 2.5596 | 4.05 |
| 28 | 35.816 | 2.5051 | 3.53 |
| 29 | 37.415 | 2.4016 | 9.57 |
| 30 | 38.149 | 2.3571 | 3.52 |
| 31 | 38.640 | 2.3282 | 12.07 |
| 32 | 39.235 | 2.2943 | 0.97 |
| 33 | 40.099 | 2.2468 | 4.45 |
| 34 | 41.662 | 2.1661 | 1.48 |
| 35 | 42.384 | 2.1308 | 2.97 |
| 36 | 43.234 | 2.0909 | 1.42 |
| 37 | 43.868 | 2.0621 | 6.45 |

AGOMELATINE HYDROCHLORIDE HYDRATE AND PREPARATION THEREOF

TECHNICAL FIELD

The present invention relates to an agomelatine hydrochloride hydrate, preparation and use thereof, and to pharmaceutical composition containing it.

TECHNICAL BACKGROUND

Agomelatine, or N-[2-(7-methoxy-1-naphthyl)pethyl]-acetamide, has the structure of formula II. It is marketed under the trade name of Valdoxan by the French company Servier as a melatonin agonist and antagonist of $5HT_{2C}$ receptor. It is the first melatonin type anti-depressant, indicated for depression, improving sleep and sexual function.

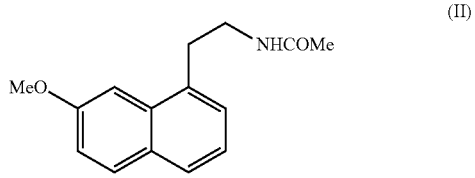

(II)

In view of its pharmaceutical value, it is important to produce the compound or a complex thereof with better purity, solubility and reproducibility.

SUMMARY OF THE INVENTION

The object of the present invention is to provide an agomelatine hydrochloride hydrate featuring excellent solubility, stability and purity, making it favourable for use in the manufacture of pharmaceutical formulations containing agomelatine.

When the present inventors attempted to purify agomelatine product, we surprisingly found that agomelatine can form a physically and chemically stable agomelatine hydrochloride hydrate when mixed with hydrocholoric acid (HCl). Said agomelatine hydrochloride hydrate is suitable for the manufacture of pharmaceutical formulations. When other conventional inorganic acids (such as sulphuric acid, phosphoric acid, perchloric acid) or organic acids (such as acetic acid, oxalic acid, tartaric acid, fumaric acid) were used, it was not easy to produce a hydrate or hydrates with unstable physical and chemical properties were obtained.

The present invention provides an agomelatine hydrochloride hydrate with the following structure of formula I:

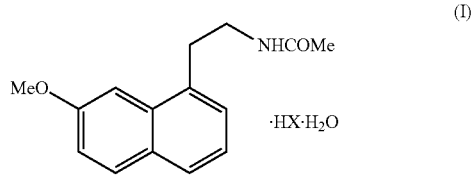

(I)

wherein X is Cl.

The present invention further provides a method for the preparation of said agomelatine hydrochloride hydrate, wherein agomelatine is reacted with HCl in any form to produce the agomelatine hydrochloride hydrate. There can be two processes: agomelatine can be dissolved in aqueous organic solvent before HCl gas is bubbled through and the precipitated crystal is rinsed and dried; or agomelatine can be added to a solution containing HCl and then the precipitated crystal is rinsed and dried. The results from repeated experiments show that in the first method, the oversupply of HCl only results in lower yield, while in the second method, it is easier to control the amount of HCl in the solvent. Therefore, the second method is preferred.

Specifically, agomelatine can also be added to an aqueous organic solvent before a solvent containing HCl is added dropwise, and the precipitated crystal is rinsed and dried.

Alternatively, agomelatine is dissolved in organic solvent before aqueous HCl solution is added dropwise, and the precipitated crystal is rinsed and dried.

The reaction temperature in the present invention can be conventional temperatures for such reactions in the art as long as it is lower than the boiling point of the solvent. In order to increase yield, room temperature or below is preferred, a temperature below the room temperature is more preferred, and 0-20° C. is most preferred.

In the above-mentioned preparation method for said agomelatine hydrochloride hydrate, the organic solvent is not specifically limited so long as it can dissolve the starting materials agomelatine and HCl and meanwhile allows said agomelatine hydrochloride hydrate to be precipitated. Suitable solvent can be used includes ethyl acetate, methyl acetate, n-butyl acetate, acetone, acetonitrile and the like, and ethyl acetate is preferred. Organic solvents with higher polarity such as alcohols (ethanol and methanol etc.), DMF, DMSO are less preferred.

The present invention is advantageous in that the inventors found that among so many conventional acids, agomelatine can react with HCl to form a stable agomelatine hydrochloride hydrate, the physical properties of which, such as stability, solubility, and hygroscopicity, are better than those products of agomelatine with any other conventional acid. The process is also less complicated than if other acid is used.

The agomelatine hydrochloride hydrate produced according to the present method has significant increased solubility than agomelatine per se, and therefore is more suitable for manufacturing pharmaceutical formulations. The product enjoys higher stability, purity and solubility. In addition, product with high purity can be obtained through a simple process, free of any complicated steps.

Pharmacological tests of the agomelatine hydrochloride hydrate demonstrated that it can be used for the treatment of melatoninergic system disorders, sleep disorders, stress, anxiety, seasonal affective disorder, major depression, cardiovascular diseases, digestive system diseases, insomnia and fatigue caused by jet lag, schizophrenia, phobia or depression disorders.

The present invention further provides a pharmaceutical composition, comprising an agomelatine hydrochloride hydrate of the invention in associated with pharmaceutically acceptable adjuvants or excipients.

The pharmaceutical composition can be formulated for various routes of administration, especially for oral administration or for injection.

The useful dosage can be adjusted depending on the nature and severity of the diseases to be treated, the mode of administration, and age and weight of the patients. The daily dosage varies from 0.1 mg to 1 g and may be administrated in a single dose or in several divided doses.

BRIEF DESCRIPTION OF DRAWINGS

Representative examples of the present invention are illustrated with the drawings in order to better convey the objects, features, and advantages of the present invention.

EXAMPLES

Example 1

Figure 1:
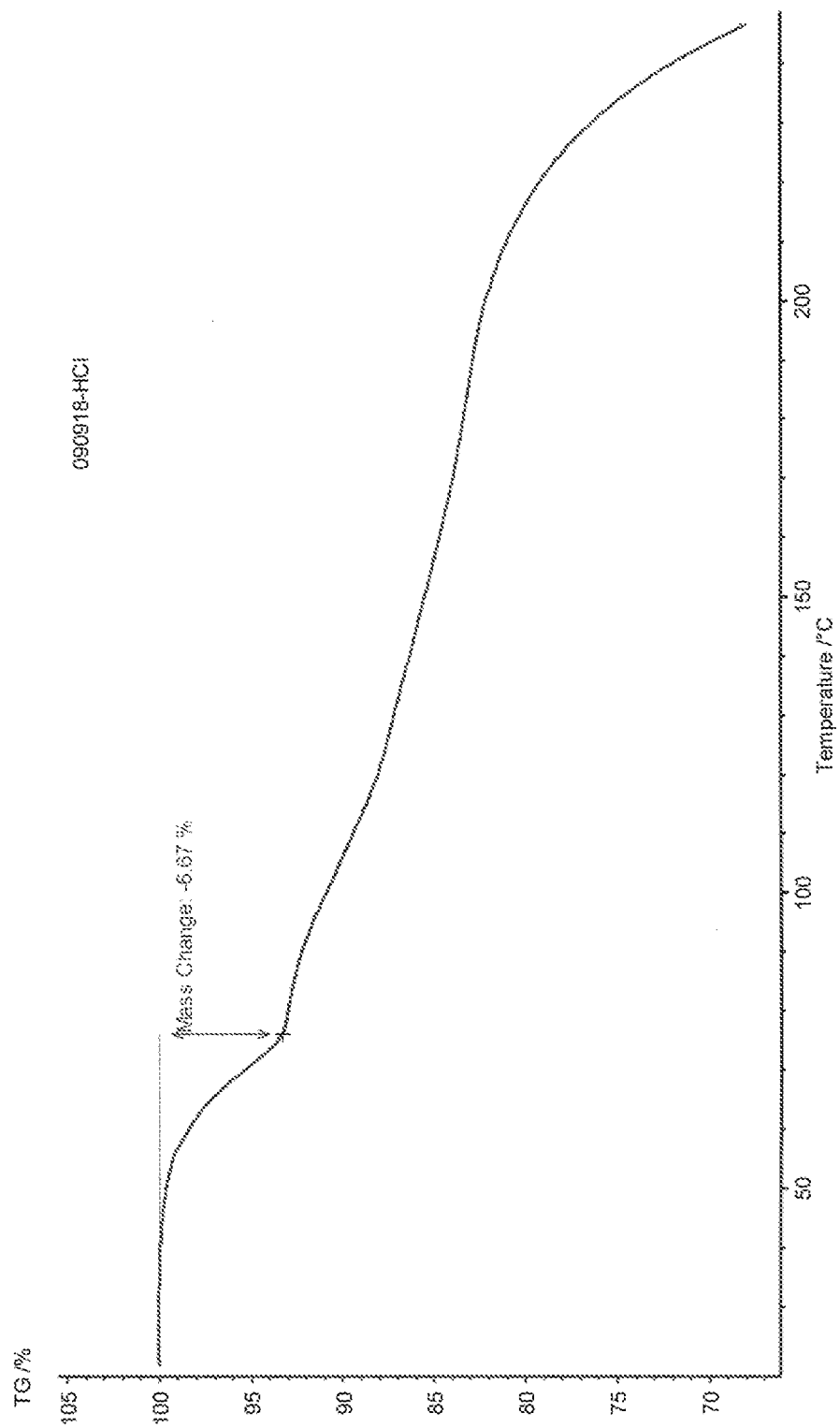
FIG. 1 shows the TGA thermogram of the product of Example 1 in the present invention.
Figure 2A:
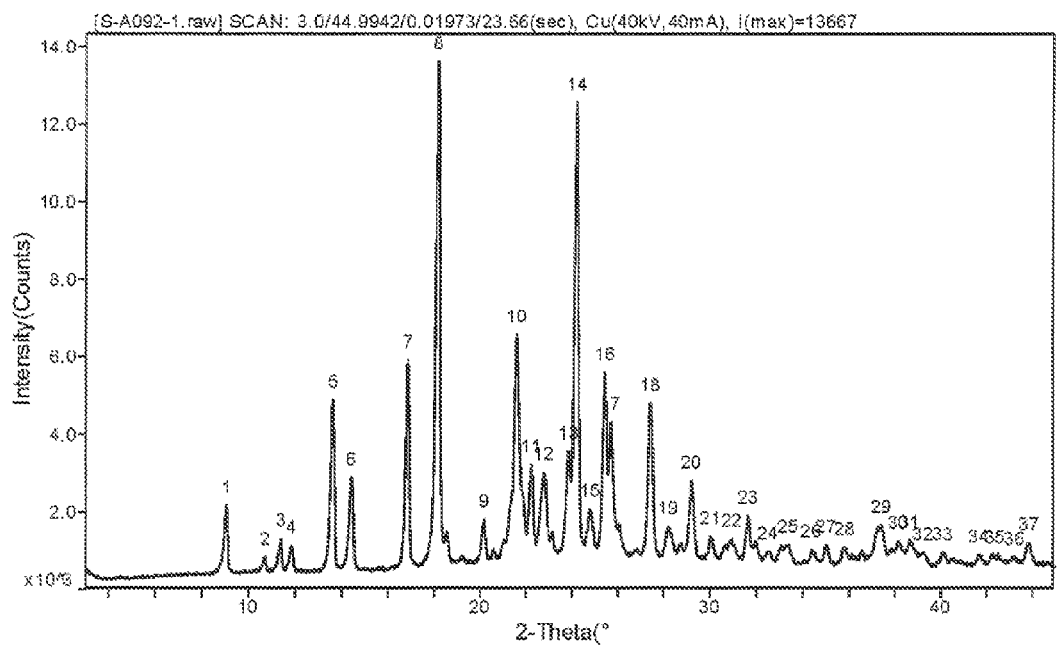
FIG. 2 shows the X-ray powder diffraction pattern of the product of Example 7 in the present invention.

1 g of agomelatine was added to 20 ml of EtOAc, 0.5 g aqueous HCl solution (36%) was added dropwise at 10° C. The mixture was stirred for 1 h, and then filtered, and the solid was rinsed twice with 2 ml of EtOAc and dried at 40° C. to afford 1 g of white solid (purity: 99.9%; yield: 81.7%).
Elemental analysis for Cl:
Calculated: Cl % (11.91 wt %)
Found: Cl % (11.88 wt %)
Mp: 88-90° C.

Example 2

10 g of agomelatine was added to 100 ml of EtOAc, and 4.6 g of aqueous HCl solution (36%) was added dropwise at 10° C. The mixture was stirred for 1 h, and then filtered, and the solid was rinsed twice with 10 ml of EtOAc and dried at 40° C. to afford 10.2 g of white solid (purity: 99.8%; yield: 88.7%).
Elemental analysis for Cl:
Calculated: Cl % (11.91 wt)
Found: Cl % (11.86 wt %)
Mp: 88-90° C.

Example 3

1 g of agomelatine was dissolved in 10 ml of EtOAc under stirring, and concentrated $H_2SO_4$ was added dropwise at room temperature. No solid precipitated during the entire process.

Example 4

1 g of agomelatine was dissolved in 10 ml of EtOAc under stirring, and concentrated $H_2SO_4$ was added dropwise at −10° C. No solid precipitated during the entire process.

Example 5

1 g of agomelatine was dissolved in 10 ml of EtOAc under stirring, and glacial acetic acid was added dropwise at −10° C. No solid precipitated during the entire process.

Example 6

1 g of agomelatine was dissolved in 10 ml of EtOAc under stirring, and fumaric acid was added dropwise at −10° C. No solid precipitated during the entire process.

Example 7

100 g of agomelatine was added to 1 L of EtOAc, and 50 g of aqueous HCl solution (36%) was added dropwise at 10° C. The mixture was stirred for 1 h, and then filtered, and the solid was rinsed twice with 100 ml of EtOAc and dried at 40° C. to afford 101 g of white solid (purity: 99.7%; yield: 82.5%).
Elemental analysis for Cl:
Calculated: Cl % (11.91 wt %)
Found: Cl % (11.86 wt %)
Mp: 87-89° C.

Agomelatine used in the above examples is commercially available or can be prepared according to methods known in the art.

Example 8

Pharmaceutical Composition

| Formulation for the preparation of 1000 capsules each containing a dose of 25 mg (agomelatine) | |
| --- | --- |
| Compound of Example 7 | 30.5 g |
| Lactose (Spherolac 100) | 82.2 g |
| Starch 1500 | 25.5 g |
| CMS-Na | 8.5 g |
| Ac-Di-Sol ® (FMC) | 17 g |
| Stearic Acid | 3.4 g |

Detection Methods and Results

1. Purity of Samples

Chromatographic conditions: C18 column; mobile phase: 10 mmol/L phosphate buffer (adjusted to pH 7.0 with NaOH): acetonitrile=2:7 (v/v); column temperature: 40° C.; detection wavelength: 220 nm; internal standard method was used on the products of Examples 1 and 2.

Solutions of the products at 1 mg/mL were prepared with the mobile phase. 10 μL of each solution was injected into the liquid chromatograph system and chromatograms were recorded. The results of the purity are shown in Examples 1 and 2.

2. Stability Test

Some of the product of Example 1 was placed in an incubator at 40° C. for 30 days to determine its stability with HPLC. The results are shown in the following table 1.

TABLE 1

| Product of Example 1 | Day 0 | Day 5 | Day 10 | Day 30 |
| --- | --- | --- | --- | --- |
| AG · HCl · H₂O | 99.6% | 99.5% | 99.5% | 99.5% |

AG = Agomelatine $C_{15}H_{17}NO_2$

3. Water Solubility

Using external standard method, the product of Example 1 was tested with HPLC, compared with agomelatine crystalline form II. The results are shown in the following table 2.

TABLE 2

| | Agomelatine content (mg/ml) | | |
| --- | --- | --- | --- |
| Sample | In water | In 0.1 N HCl | In pH 7.0 buffer |
| AG crystalline form II | 0.26 | 0.30 | 0.25 |
| AG · HCl · H₂O | 0.30 | 0.40 | 0.30 |

As can be seen, the agomelatine hydrochloride hydrate of the present invention has better solubility than agomelatine per se in water, in 0.1N HCl, which is similar to human gastric fluid, or in pH 7.0 buffer. This means the former enjoys the potential of higher bioavailability than the latter.

4. Crystal Water Analysis

Calculated water content in $C_{15}H_{17}NO_2 \cdot HCl \cdot H_2O$ is 6.06 wt %.

4.1 Fischer's Method (Appendix VIII M, Chinese Pharmacopoeia, 2010)

The product of Example 1 was analyzed according to said Fischer's method and water content was found to be 6.15 wt %.

The product of Example 7 was analyzed according to said Fischer's method and water content was found to be 6.10 wt %.

4.2 Thermal Gravity Analysis (Appendix VIII Q, Chinese Pharmacopoeia, 2010)

The product of Example 1 was analyzed according to said TGA method and water loss was found to be 6.67 wt %, meaning crystal water content in the product is 6.67 wt %. FIG. 1 shows TGA thermogram.

The measurement condition for TGA method is as follows:
Type of Instrument: NETZSCH TG 209F1
Type of Crucible: $Al_2O_3$
Flushing gas: $N_2$ 20 ml/min
Protective gas: $N_2$ 10 ml/min
Temperature range: Room temperature ~300° C.
Heat rate: 10° C./min 5. Crystal Structure Analysis The measurement condition for the X-ray powder diffraction pattern of the product of Example 7 in the present invention is as follows:
XRD parameters
Instrument Bruker D8 ADVANCE X-Ray Diffractometer
Detector LynxEye detector
X-Ray CuKα 40 kV/40 mA
Scanning Mode Theta/Theta
Monochromater Ni-filter
DivSlit 1 deg.
DivH.L.Slit 1.0 mm
Scanning Continuous Scanning from 3° to 45° with 0.02°/step
Scanning time 5 min
Scanning speed 8.0°/min
Scanning temp Room temperature The X-ray powder diffraction pattern of agomelatine hydrochloride hydrate is characterized by Bragg 2θ angle, interplanar spacing d and relative intensity (I%) as follows:

TABLE 3

| 2-Theta | d(Å) | I% |
|---|---|---|
| 9.076 | 9.7360 | 11.24 |
| 13.635 | 6.4887 | 27.62 |
| 14.427 | 6.1345 | 16.38 |
| 16.872 | 5.2507 | 34.17 |
| 18.176 | 4.8767 | 100.00 |
| 21.610 | 4.1089 | 62.25 |
| 22.259 | 3.9905 | 7.94 |
| 22.794 | 3.8981 | 19.22 |
| 23.878 | 3.7235 | 31.32 |
| 24.214 | 3.6726 | 82.40 |
| 25.457 | 3.4960 | 41.45 |
| 25.714 | 3.4617 | 37.06 |
| 27.430 | 3.2488 | 31.69 |
| 29.207 | 3.0551 | 13.75 |

When the crystal of the present invention is measured by X-ray diffraction, there may be measurement errors for the recorded peaks sometimes due to the equipment or conditions applied. Specifically, for example, the 2θ value has sometimes an error of about ±0.2, and has sometimes an error of about ±0.1 even if very precise technical equipment is used. Therefore, the measurement error should be taken into account when identifying the structure of each crystal.

6. Stability Test of the Agomelatine Hydrochloride Hydrate

The method for stability test as described in Chinese Pharmacopoeia was used in this test.
1) Affecting factors test (in open container for 10 days): high temperature (60° C.), photostability under strong light (45001×), high humidity (92.5% RH at 25° C.)
2) Accelerated test (in closed container for 6 months): at 40° C., humidity: 75% RH
3) Long-term test (in closed container for 9 months): at 25° C., humidity: 60% RH The results are shown in the following table 4.

TABLE 4

| Sample | | Water (6.10%) | Cl (11.86%) | Agomelatine hydrochloride hydrate of Example 7 (initial purity: 99.72%) |
|---|---|---|---|---|
| Affecting factors | High temperature | 1.00 | 1.75 | 99.51 |
| | Strong light | 5.95 | 11.48 | 99.67 |
| | High humidity | 6.03 | 11.63 | 99.73 |
| Accelerated test | | 6.02 | 11.65 | 99.64 |
| Long-term test | | 6.00 | 11.53 | 99.74 |

Therefore, except that water content and Cl content of agomelatine hydrochloride hydrate are decreased under a very severe condition, agomelatine hydrochloride hydrate is stable under other conditions, particularly in accelerated test and long-term test, which is favourable for use in pharmaceutical formulations.

The invention claimed is:
1. An agomelatine hydrochloride hydrate of formula I:

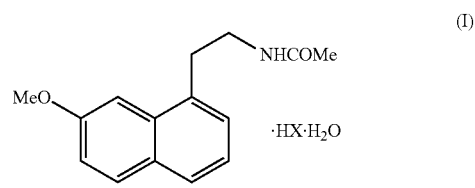

wherein X is Cl and wherein the agomelatine hydrochloride hydrate is in a crystalline form having the following X-ray powder diffraction diagram expressed in terms of Bragg 2θ angle, interplanar spacing d and relative intensity:

| 2-Theta | d (Å) | Relative Intensity (I%) |
|---|---|---|
| 9.076 | 9.7360 | 11.24 |
| 13.635 | 6.4887 | 27.62 |
| 14.427 | 6.1345 | 16.38 |
| 16.872 | 5.2507 | 34.17 |
| 18.176 | 4.8767 | 100.00 |
| 21.610 | 4.1089 | 62.25 |
| 22.259 | 3.9905 | 7.94 |
| 22.794 | 3.8981 | 19.22 |
| 23.878 | 3.7235 | 31.32 |
| 24.214 | 3.6726 | 82.40 |
| 25.457 | 3.4960 | 41.45 |
| 25.714 | 3.4617 | 37.06 |
| 27.430 | 3.2488 | 31.69 |
| 29.207 | 3.0551 | 13.75 | including crystals whose peak diffraction angles match within an error of ±0.2°.

2. A method for the preparation of the agomelatine hydrochloride hydrate according to claim 1, wherein agomelatine is reacted with HCl to produce the agomelatine hydrochloride hydrate.

3. The method according to claim 2, wherein agomelatine is reacted with HCl in an aqueous organic solvent to produce the agomelatine hydrochloride hydrate.

4. The method according to claim 3, wherein agomelatine is dissolved in an organic solvent before an aqueous HCl solution is added to precipitate a crystal of the product.

5. The method according to claim 4, wherein the aqueous HCl solution is added dropwise.

6. The method according to claim 3, wherein agomelatine is added to an aqueous organic solvent containing HCl to precipitate a crystal of the product.

7. The method according to claim 4, further comprising rinsing and drying the solid after crystallisation.

8. The method according to claim 4, wherein the reaction temperature is 0-20° C.

9. The method according to claim 4, wherein the organic solvent is ethyl acetate, methyl acetate, n-butyl acetate, acetone or acetonitrile.

10. The method according to claim 9, wherein the organic solvent is ethyl acetate.

11. The method according to claim 6, further comprising rinsing and drying the solid after crystallisation.

12. The method according to claim 6, wherein the reaction temperature is 0-20° C.

13. The method according to claim 6, wherein the organic solvent is ethyl acetate, methyl acetate, n-butyl acetate, acetone or acetonitrile.

14. The method according to claim 13, wherein the organic solvent is ethyl acetate.

15. A pharmaceutical composition, comprising the agomelatine hydrochloride hydrate according to claim 1 in combination with one or more pharmaceutically acceptable adjuvants or excipients.

16. A method of treating a condition selected from sleep disorders, stress, anxiety, major depression, and depression disorders in a subject in need thereof, comprising administration of an effective amount of the agomelatine hydrochloride hydrate according to claim 1.

* * * * *